US 6,587,538 B2

(12) United States Patent
Igarashi et al.

(10) Patent No.: US 6,587,538 B2
(45) Date of Patent: Jul. 1, 2003

(54) DETECTOR UNIT, X-RAY COMPUTER TOMOGRAPHIC PHOTOGRAPHING DEVICE, X-RAY DETECTOR, AND X-RAY DETECTOR MANUFACTURING METHOD

(75) Inventors: Kenji Igarashi, Yokohama (JP); Hideki Ide, Yokohama (JP); Kenji Ushimi, Naka-gun (JP); Yasuo Saito, Nasu-gun (JP); Yuuzo Yoshida, Otawara (JP); Miwa Okumura, Nasu-gun (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 09/990,335

(22) Filed: Nov. 23, 2001

(65) Prior Publication Data

US 2002/0064252 A1 May 30, 2002

(30) Foreign Application Priority Data

Nov. 27, 2000 (JP) ........................................ 2000-360062

(51) Int. Cl.⁷ .................................................. A61B 6/00
(52) U.S. Cl. ............................ 378/19; 378/4; 378/149; 250/367
(58) Field of Search ........................... 378/4, 7, 19, 147, 378/149, 154; 250/370.09, 367, 363.01, 363.02, 363.08

(56) References Cited

U.S. PATENT DOCUMENTS

| 4,338,521 A | * | 7/1982 | Shaw et al. ................. 250/367 |
| 4,563,584 A | * | 1/1986 | Hoffman et al. ............. 250/367 |
| 4,982,096 A | * | 1/1991 | Fujii et al. ................... 250/367 |
| 5,487,098 A | * | 1/1996 | Dobbs et al. ................. 378/19 |
| 5,781,606 A | * | 7/1998 | Dobbs et al. ................. 378/19 |
| 5,991,357 A | * | 11/1999 | Marcovici et al. ............ 378/19 |
| 6,396,898 B1 | * | 5/2002 | Saito et al. ................... 378/19 |

FOREIGN PATENT DOCUMENTS

| JP | 10-104359 | 4/1998 |
| JP | 10-239442 | 9/1998 |
| JP | 11-295432 | 10/1999 |

OTHER PUBLICATIONS

U.S. patent application Ser. No. 09/983324, filed Oct. 24, 2001, pending.

* cited by examiner

Primary Examiner—Drew A. Dunn
(74) Attorney, Agent, or Firm—Oblon, Spivak, McClelland, Maier & Neustadt, P.C.

(57) ABSTRACT

A detector unit for detecting X rays passed through a collimator having a plurality of collimator single plates, includes a substrate attached to a collimator support for supporting the collimator, a photodetecting device array including photodetecting devices mounted on the substrate, a scintillator block arranged corresponding to the photodetecting device array and provided on the photodetecting device array to convert the X rays into light, and an engaging component having an engaging portion provided on the collimator single plate side of the substrate, and engaged with the collimator single plate to regulate a position of the photodetecting device array or the scintillator block in a channel direction with respect to the collimator single plate.

9 Claims, 9 Drawing Sheets

DETECTOR UNIT, X-RAY COMPUTER TOMOGRAPHIC PHOTOGRAPHING DEVICE, X-RAY DETECTOR, AND X-RAY DETECTOR MANUFACTURING METHOD

CROSS-REFERENCE TO RELATED APPLICATIONS

This application is based upon and claims the benefit of priority from the prior Japanese Patent Application No. 2000-360062, filed Nov. 27, 2000, the entire contents of which are incorporated herein by reference.

BACKGROUND OF THE INVENTION

1. Field of the Invention

The present invention relates to a detector unit incorporated in an X-ray computer tomographic photographing device (hereinafter referred to as "X-ray CT device"), an X-ray CT device, an X-ray detector and an X-ray detector manufacturing method. More particularly, it relates to a device capable of positioning the detector unit at a desired place with respect to a collimator for removing scattered X rays.

2. Description of the Related Art

With request for higher resolution and definition of an X-ray CT image, the use of a multislicing type X-ray CT device has become frequent, and it has been put to practical use. In this X-ray CT device, the scintillator block of a solid-state detector has a two-dimensional sequence structure similar to the pattern of a photodiode. As a result, it is necessary to increase positioning accuracy concerning the arrangement of individual scintillator segments, thereby to render X rays visible in each of a plurality of detector units arrayed in a circular-arc collimator.

The adjustment of such a detector in a channel direction (i.e. the circumferential direction of the collimator) necessitates positioning such that pitches can match one another for a collimator single plate. In addition, in the above-described multislicing type X-ray CT device, highly accurate adjustments may be required not only in a channel direction but also in a slicing direction (i.e., the height direction of the collimator).

On the other hand, as a technology for obtaining an image in real time, the use of a large-area detector has been studied. However, in a currently mainstream solid-state detector, it is practically difficult to achieve a large area for a photodiode chip because of constraints imposed on a wafer size, material yield, workability, and a manufacturing device. In addition, with regard to a scintillator material, it is difficult to directly manufacture a large-area detector because of constraints imposed on an ingot size, material yield, workability, and so on.

The following problem has been discovered in the foregoing conventional multislicing type X-ray CT device. Specifically, when the detector unit is positioned with respect to the collimator, an adjustment device must be provided to perform highly accurate positioning. Thus, even when an abnormality occurs in the detector unit of a shipped X-ray CT device, and the necessity of replacing the detector unit is determined, a special device must be provided to perform highly accurate positioning, making it impossible to replace the detector unit on the spot. Consequently, the entire X-ray detector was removed from the X-ray CT device, and replaced by another.

On the other hand, in the X-ray CT device using the foregoing large-area detector, since the collimator was similarly enlarged, the warping of the collimator single plate was difficult.

BRIEF SUMMARY OF THE INVENTION

Therefore, objects of the present invention are to provide a detector unit capable of easily positioning a detector with respect to a collimator without needing any special devices, and only by mechanical assembling without being conscious of any adjustments, an X-ray CT device, and a device and a method for positioning the detector unit.

In order to achieve the foregoing object, in accordance with the invention, there is provided a detector unit for detecting X rays passed through a collimator having a plurality of collimator single plates. This detector unit comprises: a substrate attached to a collimator support for supporting the collimator; a photodetecting device array including photodetecting devices mounted on the substrate; a scintillator block arranged corresponding to the photodetecting device array, and provided on the photodetecting device array to convert the X rays into light; and an engaging component having an engaging portion provided on the collimator single plate side of the substrate, and engaged with the collimator single plate to regulate a position of the photodetecting device array or the scintillator block in a channel direction with respect to the collimator single plate.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
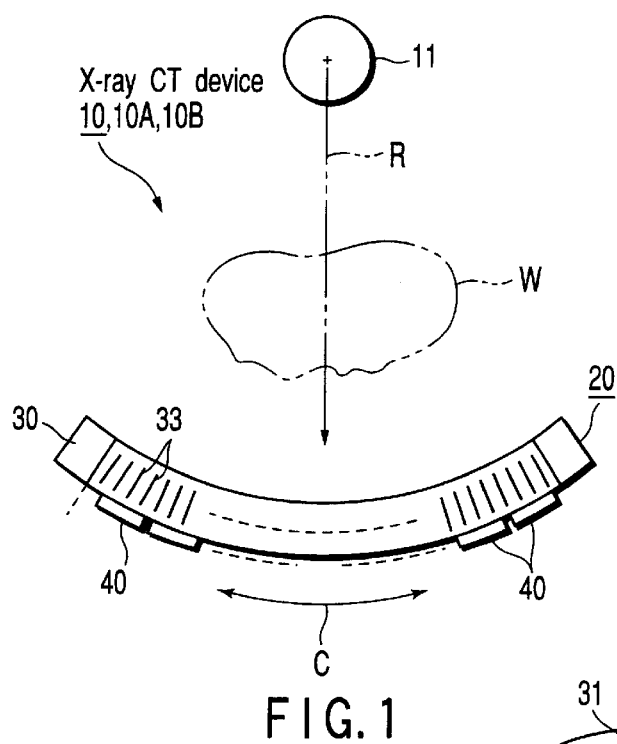
FIG. 1 is a view schematically showing an X-ray CT device incorporating an X-ray detector according to a first embodiment of the invention.
Figure 2A:
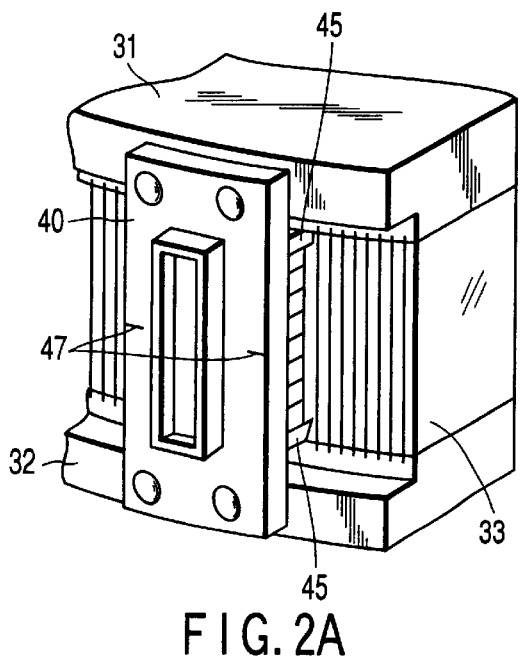
FIGS. 2A and 2B are views, each showing main portions of a detector unit incorporated in the X-ray detector.
Figure 2B:
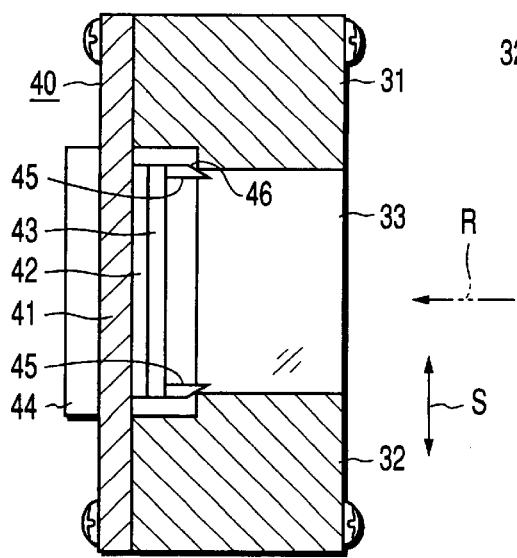

FIG. 1 shows an X-ray CT device 10 according to the first embodiment of the present invention; and each of FIGS. 2A and 2B main portions of an X-ray detector incorporated in the X-ray CT device. The X-ray CT device 10 comprises: an X-ray source 11; and the X-ray detector 20 formed in an arc shape around the X-ray source 11. In FIG. 1, reference symbol R is an irradiation direction of X rays, and W is a specimen to be inspected.

The X-ray detector 20 comprises a collimator unit 30 and a plurality of detector units 40. The detector units 40 are provided on one surface of the collimator unit 30, which does not contact the sample fluid W. The units 40 are arranged in a channel direction (i.e., the direction in which collimator single plates, which will be described later, are arranged).

The collimator unit 30 has a function for removing scattered X rays harmful to imaging, and includes: a pair of collimator supports 31 and 32 extended in the channel direction C and provided side by side in a slicing direction (i.e., the height direction of the collimator 30) S; and a plurality of collimator single plates 33 disposed between the collimator supports 31 and 32 in the channel direction C. Each collimator single plate 33 is made of a material having a high X ray absorption rate, e.g., molybdenum. When the X-ray detector 20 is incorporated in the X-ray CT detector 10, the surface of the collimator single plate 33 is arranged to be parallel to the slicing direction S, and the X-ray source 11 is positioned on the extensions of the surfaces of all the collimator single plates 33. In addition, grooves (not shown) have been are made in the opposing surfaces the collimator supports 31 and 32. The grooves are arranged in the direction of applying X rays. The collimator single plate 33 is inserted into the grooves. Accordingly, the individual collimator single plates 33 are disposed at equal pitches, thus reducing accumulated errors.

Figure 3A:
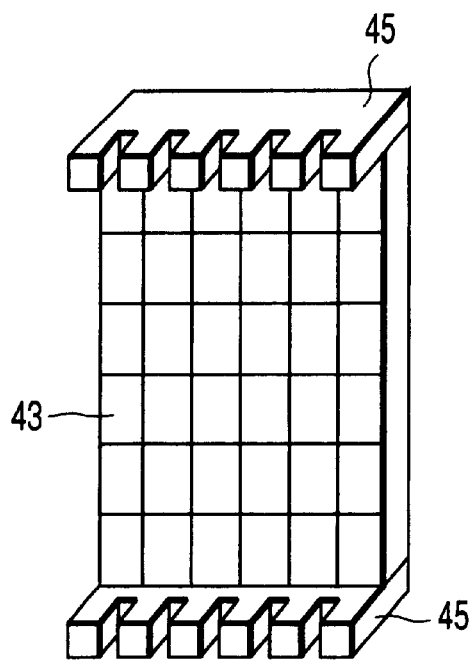
FIGS. 3A and 3B are views, each showing a scintillator and a comb-shaped adjusting component incorporated in the detector unit.
Figure 3B:
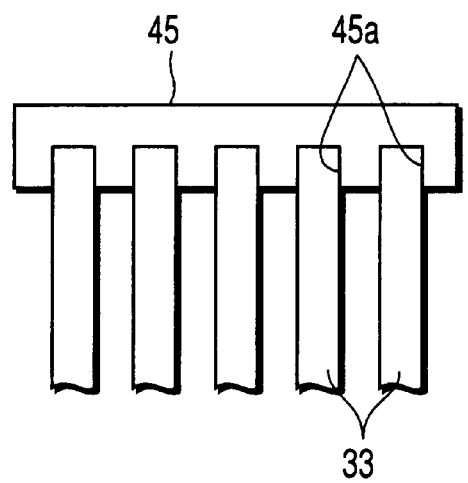

Each detector unit 40 has a function for outputting the intensity of incident X rays as an electric signal. The unit 40 comprises: a substrate 41; a photodiode chip 42 having photoelectric conversion devices arrayed on the substrate 41 in the channel and slicing directions C and S; a scintillator block 43 adapted to emit visible light by receiving X rays, a scintillator segment provided within the frame of a grid-like reflector corresponding to each incident surface of the photodiode chip 42; and a semiconductor chip (not shown) provided on the substrate 41. The semiconductor chip is configured to integrate outputs from the photodiode chip 42 and switching outputs to change a slicing thickness. A connector 44 is provided to supply the outputs of the photodiode chip 42 and semiconductor chip to an external unit (e.g., a control unit). As shown in FIG. 2B and FIGS. 3A and 3B, comb-shaped adjusting components 45 and 45 are attached to the upper and lower ends of the scintiflator block 43 in the slicing direction S.

Each comb-shaped adjusting component 45 is provided in such a manner that a concave part 45a engaging the end of the collimator single plate 33 therein is disposed on the extension of the reflector plotting the scintillator segment in the slicing direction S when seen from the irradiation direction of X rays R, and is engaged with each collimator single plate 33.

In the X-ray detector 20 constructed in the foregoing manner, the collimator single plate 33 and the detector unit 40 are aligned with each other in a manner described below.

In the detector unit 40, positioning is carried out for attachment in such a way as to dispose the concave part 45a on the slicing directions extension of the reflector of the scintillator block. Accordingly, by fitting the end of the collimator single plate 33 in the concave part 45a of the comb-shaped adjusting component 45, the collimator single plate 33 and the detector unit 40 can be easily aligned with each other. By highly accurately attaching the comb-shaped adjusting component 45 to the scintillator block 43, shifting between the collimator single plate 33 and the photodiode chip 42 or the reflector of the scintillator block 43 can be reduced to an amount to be ignored.

As shown in FIG. 2B, by defining the inner dimension of each of the collimator supports 31 and 32 sides of the comb-shaped adjusting component 45, and the outer dimension of the scintillator block 43 of the slicing direction including the comb-shaped adjusting component 45, highly accurate position can also be performed in the slicing direction. Further, a tapered part 46 is formed in the outer side face of the slicing direction of the tip of the comb-shaped adjusting component 45. Thus, a structure is provided, where when the collimator unit 30 and the detector unit 40 are fitted together, the detector unit 40 can be fitted even with slight shifting, and can also be positioned.

Moreover, the alignment of the slicing direction between adjacent detector units 40 may be carried out by providing alignment marks 47 on the backside (surface facing the collimator single plate 33) of the substrate 41 beforehand on the basis of the pattern of the scintillator block 43, and setting these alignment marks to be level with each other.

As described above, according to the X-ray CT device of the first embodiment, the detector can be easily and highly accurately positioned with respect to the collimator without needing any special devices for highly accurate positioning, and only by mechanical assembling without being conscious of adjustments. As a result, even if a trouble occurs in the detector unit 40 after the shipment of the X-ray CT device 10 as a product, the detector unit 40 can be replaced on the spot within a short time.

Figure 4A:
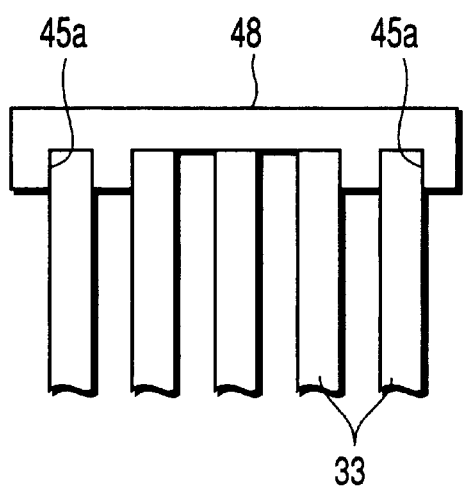
FIGS. 4A and 4B are views, each showing a modified example of the comb-shaped component.
Figure 4B:
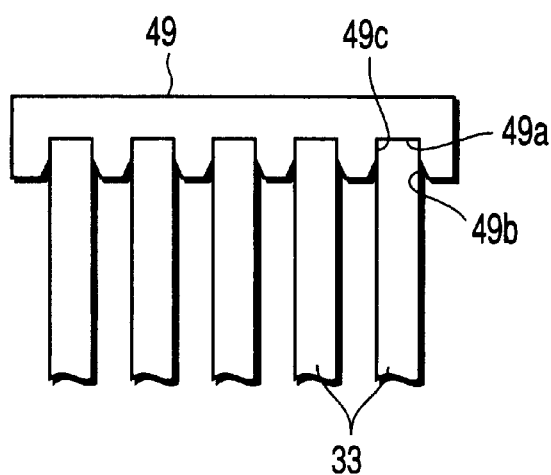

FIGS. 4A and 4B show comb-shaped adjusting components 48 and 49 as modified examples of the comb-shaped adjusting component 45. Specifically, in the comb-shaped adjusting component 48 shown in FIG. 4A, instead of forming the concave parts 48a for all the collimator single plates 33, concave parts 48a may be provided to be inserted into at least two or more collimator plates. An advantage obtained in this case is similar to the above.

In the comb-shaped adjusting component 49 shown in FIG. 4B, the tip 49b of the projection in the concave 49a is tapered with respect to the collimator single plate 33. This facilitates insertion into the collimator single plate 33, making it possible to complete assembling within a short time. In a side deeper than the tip 49b, a fitting part 49c is formed to enable highly accurate positioning.

Figure 5:
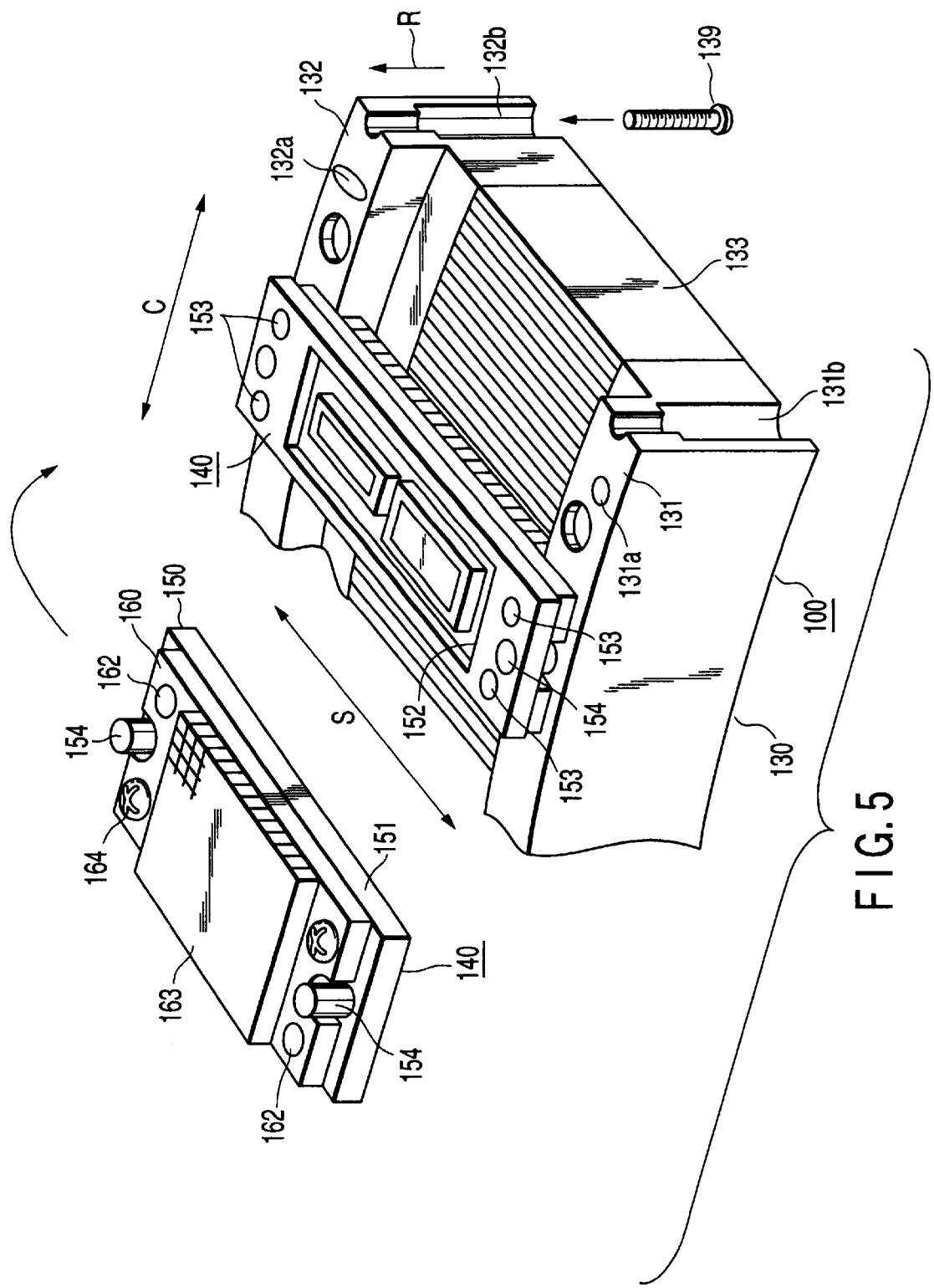
FIG. 5 is a view showing main portions of an X-ray detector according to a second embodiment of the invention.

FIG. 5 shows the main portions of an X-ray detector 100 incorporated in an X-ray CT device 10A according to the second embodiment of the invention. The X-ray detector 100 includes a collimator unit 130, and a detector unit 140 attached to the collimator unit 130 in the channel direction C.

The collimator unit 130 has a function for removing scattered X rays, and includes: a pair of collimator supports 132 and 132 disposed in the slicing direction S, and extended in the channel direction C; and a plurality of collimator single plates 133 provided side by side between the collimator supports 131 and 132 in the channel direction C. Each collimator single plate 133 is made of a material having a high X ray absorption rate, e.g., molybdenum.

When an X-ray detector 100 is incorporated in the X-ray CT device 10A, the surface of the collimator single plate 133 is arrange to be parallel to the slicing direction S, and an X-ray source 11 is positioned on the extensions of the surfaces of all the collimator single plates 133. Further, grooves (not shown) have been made in the opposing surfaces of the collimator supports 131 and 132. The grooves are arranged in the direction in which X rays are applied and the collimator single plates 133 are inserted into these grooves. Thus, the collimator single plates 133 can be manufactured at equal pitches, and by a small number of accumulated errors.

In the collimator supports 131 and 132, a round hole 131a and an oblong hole 132a are formed for inserting the pair of positioning pins 154 and 154 of a later-described positioning plate 150, with the grooves for positioning the collimator single plates 133. In addition, in the collimator supports 131 and 132, counterbore parts 131b and 132b are formed fro the X-ray source 11 sides of the collimator supports 131 and 132 in the direction applying of X rays R direction. Through-holes are provided in the counterbore parts 131b and 132b. A connecting screw 139 is inserted from the X-ray source 11 side, and the detector unit 140 can be connected and fixed by a screw hole 153 formed in the positioning plate 150.

The detector unit 140 includes a positioning plate 150, and a photodiode substrate 160. The positioning plate 150 includes a plate material 151, a window portion 152 provided in the plate material 151, screw holes 153 provided in both ends, and a pair of positioning pins 154 and 154 inserted into the plate material 150 by pressure. A semiconductor chip 155 and a connector 156 are provided on that side of the positioning plate 150, which faces away from the collimator unit 230. The semiconductor chip 155 integrates the outputs from the photodiode substrate 160 and switches outputs to change the thickness of slices. The connector 156 supplies the outputs of the photodiode substrate 160 and semiconductor chip 155 to an external unit (e.g., a control unit).

The photodiode substrate 160 having the photodiode and the scintillator block loaded is positioned in a predetermined positional relation with the pair of positioning pins 154 and 154 inserted by pressure into the positioning plate 150 by using a later-described adjusting device 180.

Figure 6A:
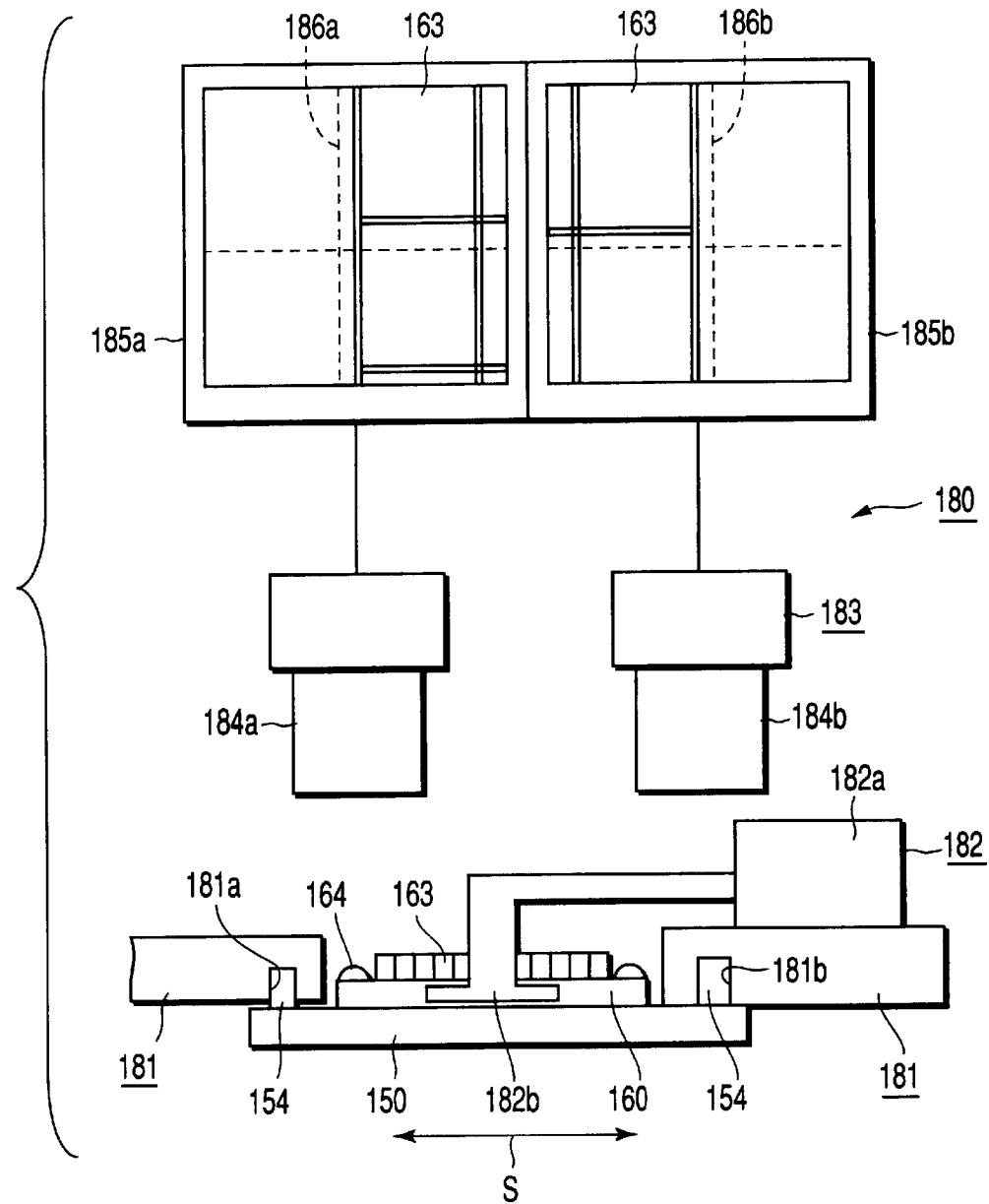
FIGS. 6A and 6B are views, each showing an assembling method of a detector unit incorporated in the X-ray detector.
Figure 6B:
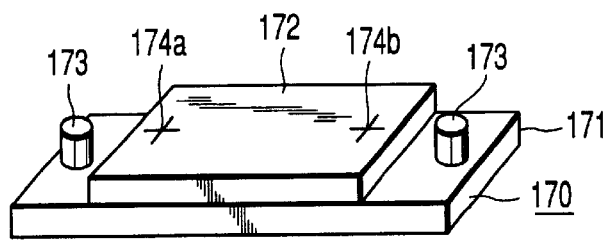

As shown in FIG. 6B, a master base 170 is composed of a plate material 171, a dummy detector pack 172 formed on the plate material 171, and a pair of pins 173 and 173. In the dummy detector pack 172, cross marks 174a and 1174b are provided to position a center axis on the basis of the pins 173 and 173. In other words, the cross marks 174a and 174b are disposed on a straight line connecting the pins 173 and 173.

FIG. 6A shows the adjusting device 180. The adjusting device 180 includes a base 181, an adjusting unit 182 and an imaging unit 183.

In the base 181, pin holes 181a and 181b are provided to insert the positioning pins 154 and 154. The adjusting unit 182 includes an XYθ adjusting mechanism 182a, and a clamping mechanism 182b driven by the XYθ adjusting mechanism 182a.

The imaging unit 183 includes CCD camera units 184a and 184b for imaging the upper surface of the positioning plate 150 from fixed points, and monitors 185a and 185b for displaying images from the CCD camera units 184a and 184b.

The X-ray detector 120 constructed in the foregoing manner is assembled in the following manner.

Specifically, cross lines 186a and 186b are set as references on the screens of the monitors 185a and 185b of the adjusting device 180. The master base 170 is attached to the base 181, and the imaging positions of the CCD camera units 184a and 184b are roughly adjusted so as to set the cross marks 174a and 174b within a visual field. Then, the cross lines 186a and 186b displayed on the monitors 185a and 185b are moved to coincide with the shown cross marks 174a and 174b.

Then, the master base 170 is removed, and the positioning plate 150 and the photodiode substrate 160 are attached by a screw 164 in a temporarily assembled state. Accordingly, a state is set again, which is similar to that when the detector unit 140 is assembled on the collimator supports 131 and 132.

Then, only the photodiode substrate 160 is gripped by the claming mechanism 182b. An adjustment is carried out in the triaxial direction of XYθ by the XYθ adjusting mechanism 182b while checking the cross lines 186a and 186b on the monitors 185a and 185b, and the scintillator block pattern of the detector pack 163.

Then, alignment is carried out so that the reflector extended in the slicing direction S and the cross lines 186a and 186b overlap each other between the scintillator segments. The amount of shifting between the cross lines 186a and 186b and the slicing direction of the scintillator block pattern is adjusted not in the manner of achieving coincidence at either one of the sides, but in a well-balance manner such that the amounts of shifting at both sides are equal to each other. After the adjustment, the photodiode substrate 160 and the positioning plate 150 are united by finally fastening the screw 164.

Thus, the photodiode substrate 160 can be fixed to the positioning plate 150 in a highly accurate positioning state with respect to the positioning pin 154.

Then, the positioning pins 154 and 154 of the detector unit 140 are inserted into the round hole 131a and the oblong hole 132a of the collimator supports 131 and 132. Since the positioning pin 154 is fitted into the round hole 131a, the detector unit 140 can be highly accurately positioned with respect to the collimator supports 131 and 132. By providing the oblong hole 132a long in the slicing direction S, the amount of shifting in the slicing direction can be permitted when a plurality of detector units 140 are arrayed in the channel direction.

As described above, according to the X-ray detector 120 of the second embodiment, the detector pack 163 is highly accurately positioned and fixed in the positioning plate 150, and the round hole 131a and the oblong hole 132a are formed in the collimator supports 131 and 132 as the attaching references with respect to the collimator single plate 133. Thus, the alignment between the detector unit 140 and the collimator supports 131 and 132 can be easily carried out by using the positioning pin 154, making it possible to deal with unexpected and sudden replacement.

The positioning of the detector pack 164 in the positioning plate 150 is executed at the production plant or the like. Thus, when the detector unit 140 of the shipped X-ray CT device is replaced by another, highly accurate assembling can be carried out without using any special devices.

Moreover, since access is allowed from the X-ray source 11 side through the counterbore parts 131b and 132b to the connecting screw 139 of the detector unit 140, no maintenance space needs to be provided in the outside of the X-ray detector 100, making it possible to miniaturize the X-ray CT device. In addition, in a place where the C-ray CT device 10A is installed, the detector unit 140 can be easily replaced by another without removing the X-ray detector 120 from the X-ray CT device 10A.

Figure 7:
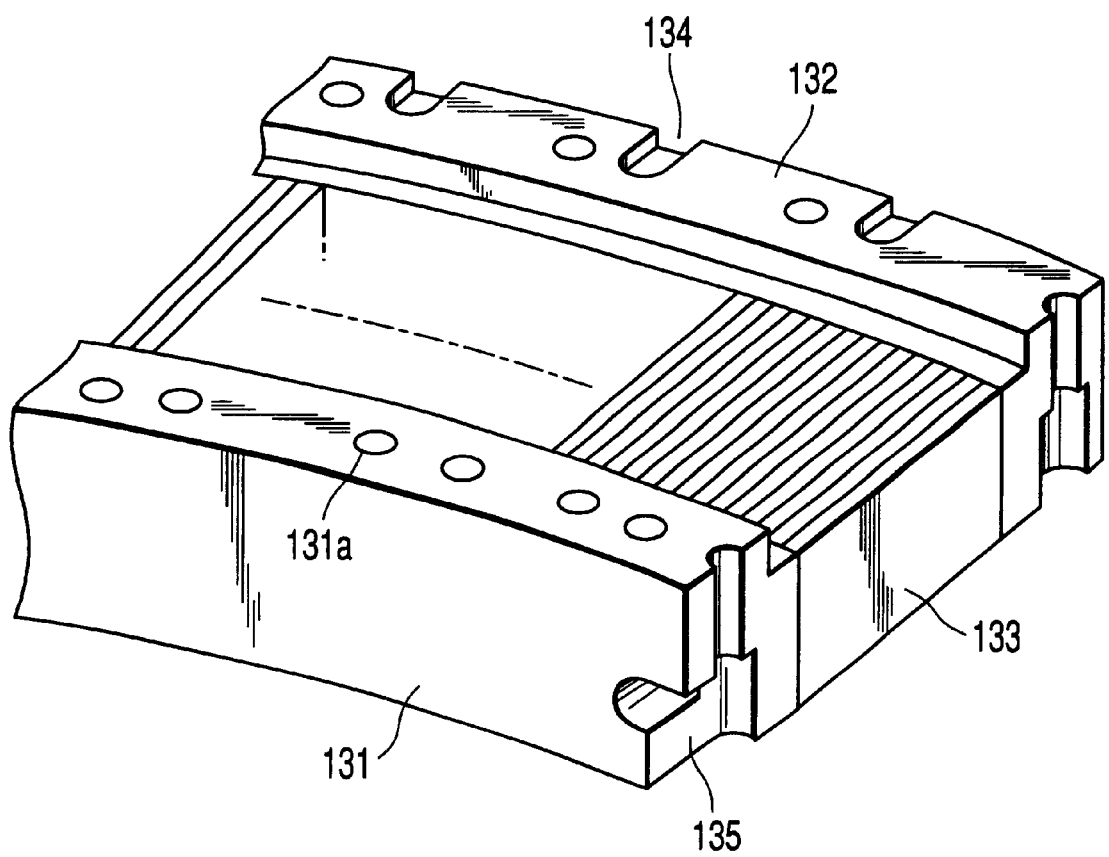
FIG. 7 is a view, showing a modified example of the X-ray detector.

FIG. 7 shows a modified example of the collimator supports 131 and 132. Instead of the oblong hole 132a long in the slicing direction, an oblong groove 134 cut from the side end surface of the collimator support 132 may be formed. In addition, instead of each of the counterbore parts 131b and 132b, a groove part 135 cut from the side end surface of the collimator support 132 may be formed.

Figure 8A:
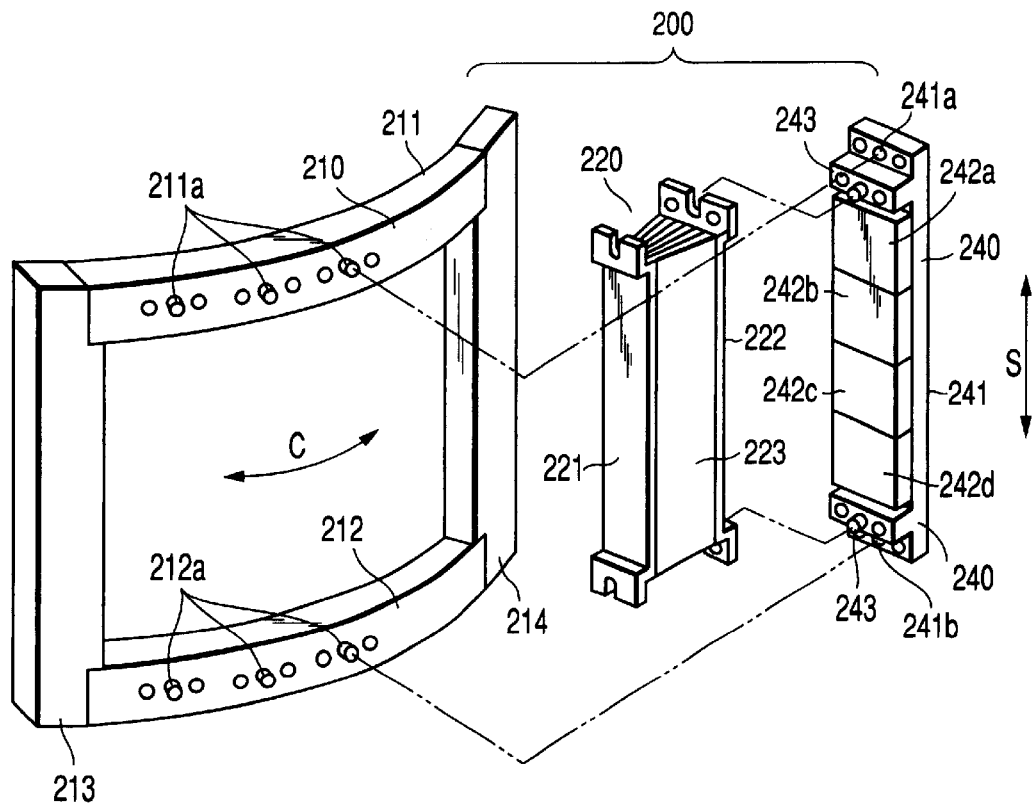
FIG. 8A is an assembling exploded view showing an X-ray detector according to a third embodiment of the invention.
Figure 8B:
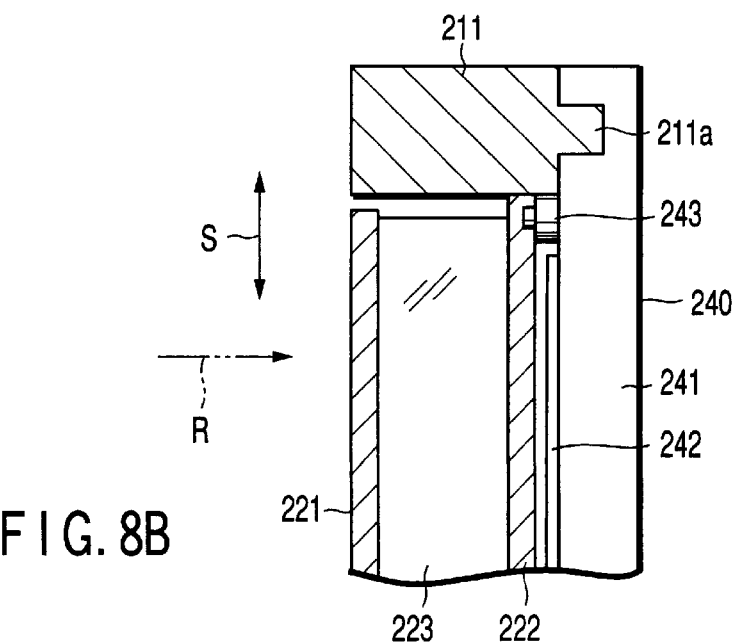
FIG. 8B is a sectional view showing main portions of the X-ray detector.

FIGS. 8A and 8B are assembling exploded and sectional views, each showing an X-ray detector incorporated in an X-ray CT device 10B according to a third embodiment of the invention. The X-ray detector 200 includes: a base 210 incorporated in the X-ray CT device; a plurality of collimator modules 220 and 230 attached to the base 210; and detector units 240 provided corresponding to the collimator modules 220 and 230.

The base 210 includes circular-arc supports 211 and 212, and support blocks 213 and 214 attached to the ends of the supports 211 and 212. In the supports 211 and 212, positioning pins 211a and 212a are provided in a projected manner.

Figure 9A:
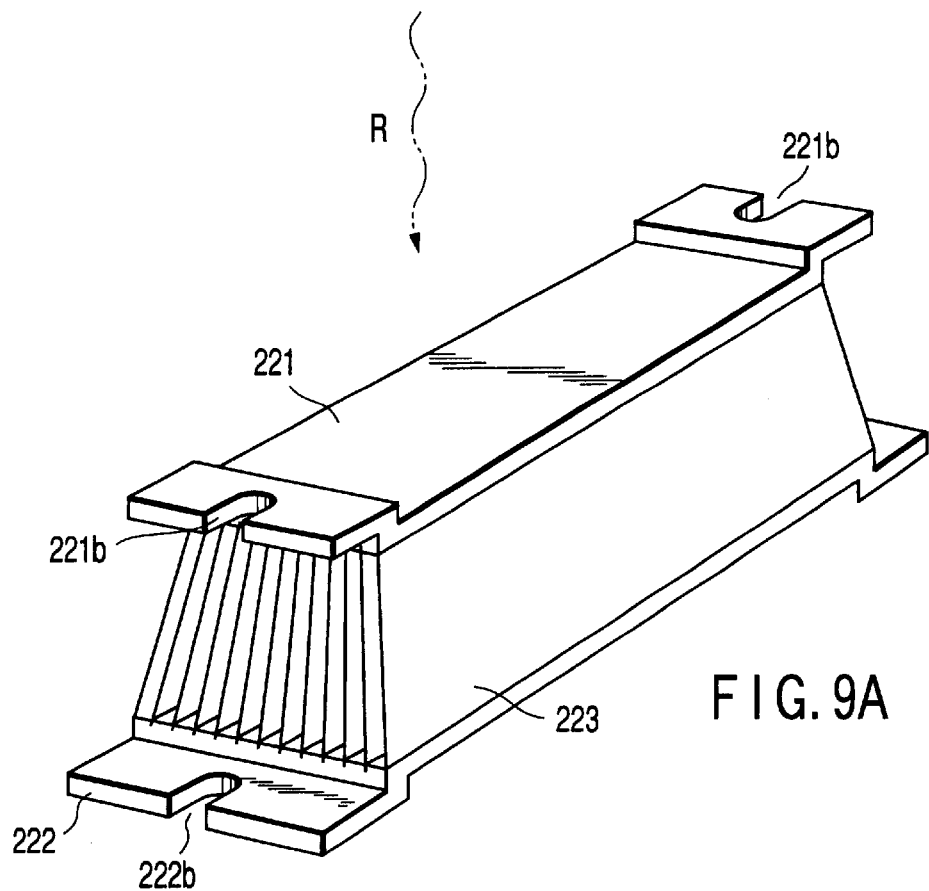
FIGS. 9A and 9B are views, each showing a collimator unit incorporated in the X-ray detector.
Figure 9B:
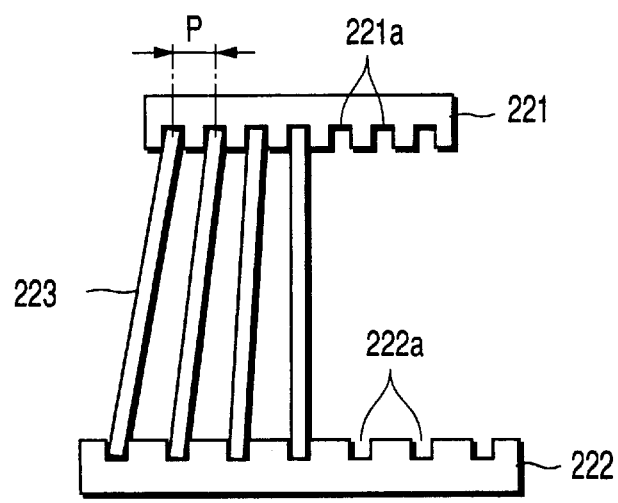
Figure 10A:
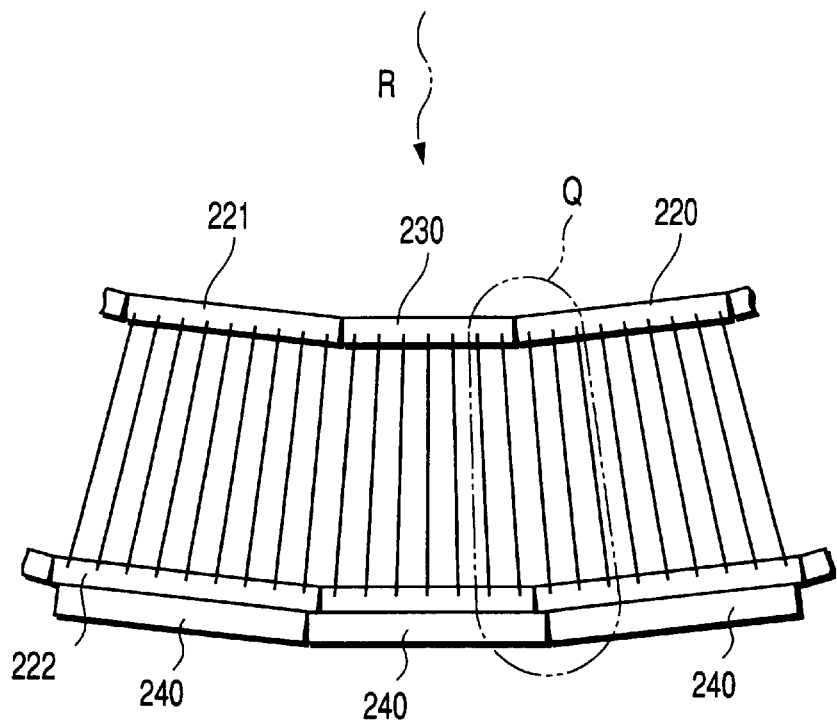
FIGS. 10A to 10C are views, each showing the collimator unit and a detector unit incorporated in the X-ray detector.

As shown in FIGS. 9A and 9B, and FIG. 10A, the collimator modules 220 and 230 include X-ray source side support 221, and a detector unit side support 222, each of which is made of a material having a high X-ray transmission factor, e.g., a carbon fiber reinforced resin (CFRP). In other words, a structure is provided, where X rays are transmitted through the supports 221 and 222 in order, and reach the detector unit 140.

Single plate inserting grooves 221a and 222a are respectively formed in the supports 221 and 222, and a collimator single plate 223 is inserted between these single plate inserting grooves 221a and 222a. Since the single plate inserting grooves 221a and 222a are shallow, less than about 1 mm, the single plate inserting grooves 221a and 222a are formed to be perpendicular to the surfaces of the supports 221 and 222. In addition, the single plate inserting groove 221a and 222a are formed to be wider than the thickness of the collimator single plate 223 and, by using adhesive to fix the inserted collimator single plate 223, the rigidity of the collimator module 220 can be maintained.

Therefore, if the supports 221 and 222 are fixed ends, and the both sides holding structure of the collimator single plate 223 is employed, a span can be shortened and, by forming the single plate inserting grooves 221a and 222a in the supports 221 and 222 sides beforehand, the advantage of correcting warping in the slicing direction S can be provided.

In addition, by setting the pitches P of the single plate inserting grooves 221a and 222a respectively provided in the supports 221 and 222 to values different from each other, the collimator single plate 223 of the assembled collimator module 220 can be radially arranged around the X-ray source 11.

Notched grooves 221b and 222b are respectively formed in the supports 221 and 222. These notched grooves 221b and 222b coincide with the positions of center ones 221a and 222a among the single plate inserting grooves 221a and 222b formed in the supports 221 and 222.

The basic structure of a collimator module 230 shown in FIG. 10 is similar to that of the collimator module 220. Reference numerals 231 and 232 denote collimator single plates. The collimator modules 220 and 230 are substantially similar to each other in structure except for the numbers of held collimator single plates. A difference in the numbers is two.

To attach the collimator modules 220 and 230 to the base 210, assembling is carried out by deciding a center position by using the respective notched grooves 221b and 222b of the supports as references. Accordingly, for the radially arranged collimator single plate 223, the X-ray source 11 is positioned on ht extension of a perpendicular line passed through the support.

Figure 10B:
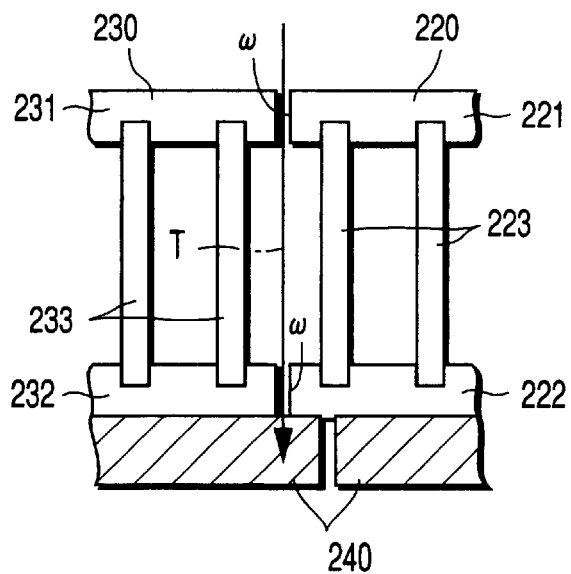

FIG. 10B is an expanded view showing a connecting portion Q between the collimator modules 220 and 230. Because of the module structure, a path is present, where X rays (double dotted chain line T) are passed through a space between the collimator modules 220 and 230 and directly made incident on the detector unit 240. Each of the supports 221 and 222 is made of a resin having a high X-ray transmission factor, e.g., a carbon fiber reinforced resin, but it does not mean that there is no X ray attenuation. As a result, when X rays having a uniform intensity distribution are radiated, as a signal detected by the detector, only a part having a space ω (may be detected as one having a high X-ray intensity.

Figure 10C:
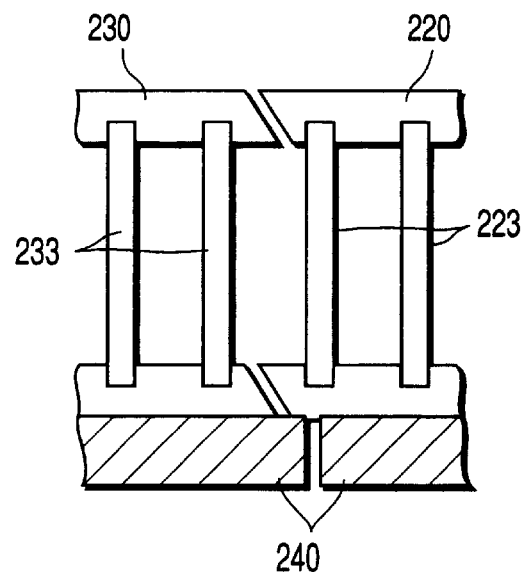

FIG. 10C shows a modified example of solving the foregoing problems. That is, both ends of the supports 221 and 222 of the large collimator module 220 are formed in tapered shapes so as to extend a foot when seen from the X-ray source 11 side, and both ends the support 232 of the small collimator module 230 are formed in tapered shapes to be fan-like when seen from the detector unit 240 side. Accordingly, X rays can be prevented from being passed through the supports 221, 222, 231 and 132 to directly reach the detector unit 240. Thus, substantially on a full surface of the detector unit 140, the occurrence of a specific X-ray intensity distribution can be prevented, and an electric signal dependent on the X-ray intensity detected by the detector unit 140 becomes uniform on the full surface of the detector unit 240. It is therefore possible to form an image without executing any special processing such as correction.

The detector unit 240 includes a module base 241, and four detector packs 242a to 142d disposed in a file in the module base 241. In the module base 241, a positioning pin 243 is provided so as to be projected.

Figure 11A:
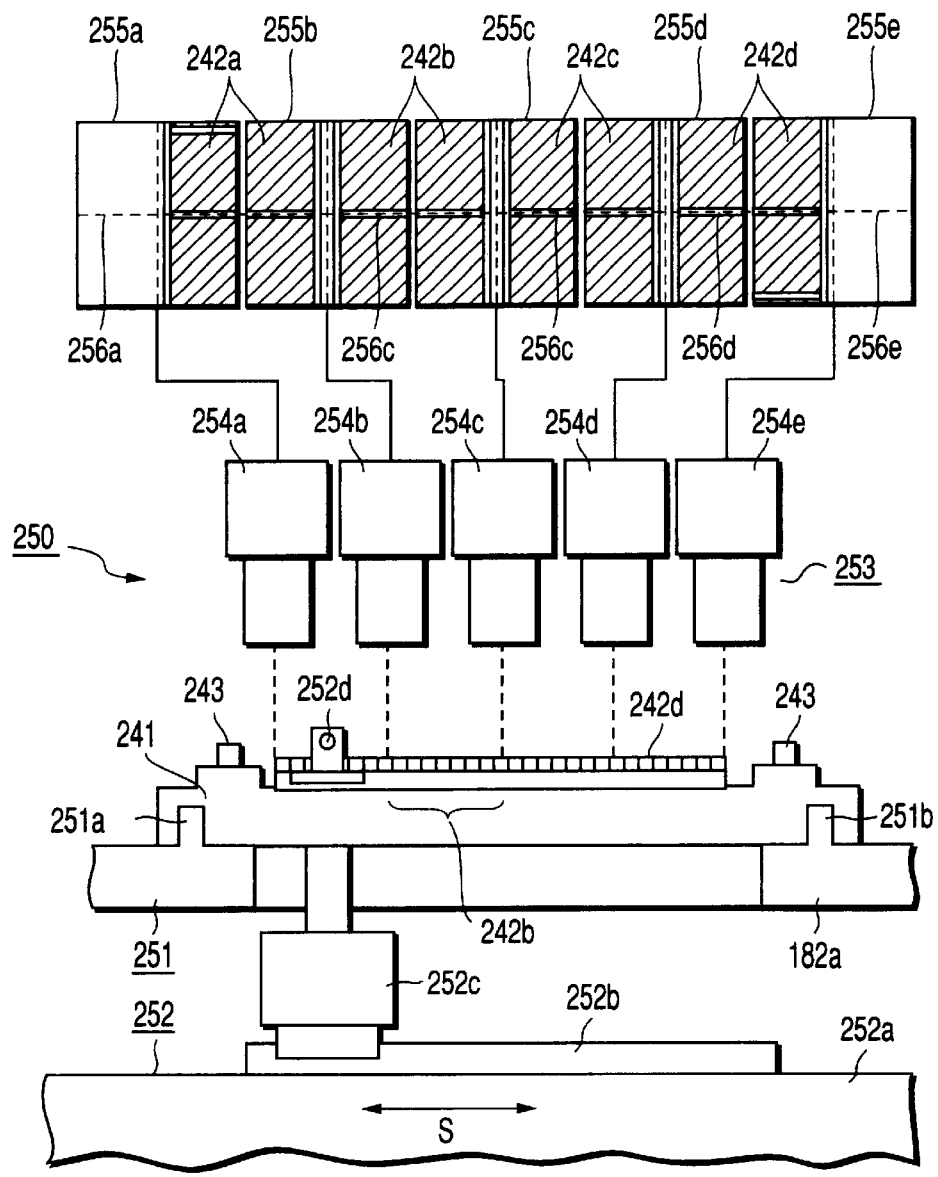
FIGS. 11A and 11B are views, each showing an assembling method of the detector unit incorporated in the X-ray detector.

FIG. 11A shows an adjusting device 150. The adjusting device 250 includes a base 251, an adjusting unit 252, and an imaging unit 253. In the base 251, pins 251a and 251b are provided. The adjusting unit 252 includes a frame 252e, a uniaxial stage 252b, an XYθ adjusting device 252c guided by the uniaxial stage 252c to reciprocate in the slicing direction S, and a clamping mechanism 252c driven by the XYθ adjusting mechanism 252c.

The imaging unit 253 includes five CCD camera units 254a to 254e for imaging both ends of the detector packs 22a to 22d from fixed points in the slicing direction S, and monitors 255a to 255e for displaying images from the CCD camera units 254a to 254e.

Figure 11B:
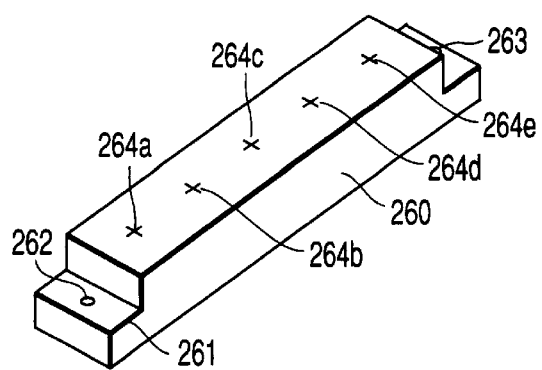

Next, a master base 260 shown in FIG. 11B will be described. The master base 260 is made of a plate material 261. In the plate material 261, a pin hole 262 and a pin hole 262 long in the slicing direction are formed for a pair of positioning pins. In addition, in the plate material 261, cross marks 264a to 264e are formed with machine accuracy so as to decide a center axis by using the pin holes 262 and 263 as references.

The X-ray detector 200 thus constructed is assembled in the following manner. Specifically, cross lines 256a to 256eare set as references on the screens of the monitors 255a to 255e of the adjusting device 150. The master base 260 is attached to the base 251, and the imaging positions of the CCD cameras 254a to 254e are roughly adjusted to contain the cross marks 264a to 264e. Further, the cross lines 256a to 256e displayed on the monitors 255a to 255e are moved so as to match the shown cross marks 264a to 264e.

The, by removing the master base 260, only the detector pack 242a is gripped by the clamping mechanism 252d. An adjustment is carried out in the triaxial direction of XYθ by the XYθ adjusting mechanism 252c while checking the cross lines 256a and 256b on the monitors 255a and 255b, and the scintillator block pattern of the detector pack 242a, and alignment is carried out such that the reflector and the cross lines 256a and 256b provided side by side in the slicing direction can be overlapped between the scintillator segments. The amounts of shifting in the slicing direction between the cross lines 256a and 256b and the scintillator block pattern are not adjusted by coincidence at either one of the sides, but adjusted such that the amounts of shifting are well-balanced and equal (identical) between both. After the adjustment, by firmly fixing a screw (not shown), the detector pack 242a and the module base 242 are united.

Similarly, the detector packs 242b to 242d can be highly accurately positioned with respect to the module base 241.

Then, the collimator module 220 is bound in the channel direction by the pins inserted by pressure into the module base 241 to allow highly accurate positioning. The positioning pins 211a and 2121a of the base 210 are fitted in the pin hole 241a and the oblong hole 241b of the module base 241 to allow highly accurate positioning.

As described above, according to the X-ray detector 200 of the third embodiment, with the employment of the large-area detector, the amount of warping can be suppressed to about several 10 μm even when a large collimator single plate, e.g., collimator single plates 223 and 233 of about 200 mm length, is used. Since the collimator module 220 and the detector module 140 can be assembled according to the same reference, the accuracy of component machining can be easily guaranteed (accumulated errors). Moreover, since the detector packs 242a to 242d can be aligned while seeing the scintillator block pattern, the highly accurately positioning of the plurality of detector packs in the slicing direction can be facilitated.

The present invention is not limited to the foregoing embodiments, but various modifications and changes can be made without departing from the teachings of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A detector module positioning method for mounting a plurality of detector modules, in a slicing direction, in a module base having a hole to be fitted around a positioning pin provided in a base extended in a channel direction, comprising the steps of:
    forming a positioning mark on a monitor screen;
    fixing the module base by fitting the hole around the positioning pin provided in the attaching base;
    imaging the module base, and displaying an image thereof on the monitor screen; and
    positioning each of the detector modules based on the positioning mark.

2. The detector module positioning method according to claim 1, wherein said positioning mark forming step includes:
    a step of imaging a master base having a hole fitted around the positioning pin provided in the base, and a reference point having a highly accurately defined positional relation with a reference point corresponding to the hole and the detector module, and then displaying the resultant image on the monitor screen, and
    a step of forming the positioning mark in a position of the reference point.

3. A detector unit for detecting X rays which have passed through a collimator having a plurality of collimator single plates, comprising:
    a scintillator configured to convert the X rays into light;
    a photodetecting device array configured to detect the light produced from the scintillator;
    a substrate holding the photodetecting device array mounted thereon and attached to a collimator support configured to support the collimator single plates, the substrate having a back surface and a side surface on one of which markings are formed; and
    the markings indicating height positions as measured in a slicing direction along a height of the substrate and the markings being determined with one of the photodetecting device array and the scintillator block as a reference.

4. An X-ray computer tomographic photographing device for obtaining a tomographic image of a specimen, comprising:
    an X-ray source configured to irradiate the specimen with X rays; and
    an X-ray detector disposed on a side opposite to that of the X-ray source, with the specimen being located therebetween, said X-ray detector including,
    a plurality of collimator single plates,
    a collimator support configured to support the collimator single plates, and
    the detector unit of claim 3 attached to the collimator support member after being positioned.

5. An X-ray computer tomographic photographing device for obtaining a tomographic image of a specimen, comprising:
    an X-ray source configured to irradiate the specimen with X rays; and
    an X-ray detector disposed on a side opposite to that of the X-ray source, with the specimen being located therebetween, said X-ray detector including,
    a plurality of collimator single plates arranged radially, with the X-ray source as a center,
    a collimator module comprising an incident side support and an emission side support,
    the incident side support being provided with insertion grooves in which the collimator single plates are inserted,
    the emission side support being provided with insertion grooves in which the collimator single plates are inserted,
    the insertion grooves of the emission side support having a pitch different from that of the insertion grooves of the incident side support such that the X-ray source is located at a position on imaginary extensions of the collimator single plates, and
    a detector unit configured to detect X rays which have passed through gaps defined between the collimator single plates.

6. The X-ray computer tomographic photographing device according to clam 5, further comprising:
    a plurality of collimator modules each being similar in structure to said collimator module; and incident side supports of adjacent ones of the collimator modules having opposing surfaces that intersect with a traveling direction of the X rays.

7. An X-ray computer tomographic photographing device for obtaining a tomographic image of a specimen, comprising:

an X-ray source configured to irradiate the specimen with X rays; and an X-ray detector disposed on a side opposite to that of the X-ray source, with the specimen being located therebetween, said X-ray detector including, a plurality of collimator single plates arranged radially, with the X-ray source as a center, a collimator support provided with insertion grooves in which the collimator single plates are inserted, the insertion grooves being formed to extend in a traveling direction of the X rays such that the X-ray source is located at a position on imaginary extensions of the collimator single plates; and a detector unit configured to detect X rays which have passed through gaps defined between the collimator single plates.

8. An X-ray computer tomographic photographing device for obtaining a tomographic image of a specimen, comprising:

an X-ray source configured to irradiate the specimen with X rays; and an X-ray detector disposed on a side opposite to that of the X-ray source, with the specimen being located therebetween, said X-ray detector including, a pair of collimator supports which face each other in a slicing direction along a distance between the collimator supports and which extend in a channel direction receiving said X rays, one of the collimator supports being provided with a plurality of round holes formed at a predetermined pitch and arranged in the channel direction, another one of the collimator supports being provided with a plurality of elongated holes elongated in the slicing direction, formed at the predetermined pitch, and arranged in the channel direction, a plurality of collimator single plates located between the collimator supports and juxtaposed in the channel direction, and a detector unit configured to detect X rays which have passed through gaps between the collimator single plates, the detector unit being provided with positioning pins fitted in the round holes and positioning pins inserted in the elongated holes.

9. An X-ray computer tomographic photographing device for obtaining a tomographic image of a specimen, comprising:

an X-ray source configured to irradiate the specimen with X rays; and an X-ray detector disposed on a side opposite to that of the X-ray source, with the specimen being located therebetween, said X-ray detector including, a pair of collimator supports which face each other in a slicing direction along a distance between the collimator supports and which extend in a channel direction receiving said X rays, one of the collimator supports being provided with a plurality of round holes formed at a predetermined pitch and arranged in the channel direction, another one of the collimator supports being provided with a plurality of elongated grooves which are formed in a side surface thereof, elongated in the slicing direction, formed at the predetermined pitch, and arranged in the channel direction, a plurality of collimator single plates located between the collimator supports and juxtaposed in the channel direction, and a detector unit configured to detect X rays which have passed through gaps between the collimator single plates, the detector unit being provided with positioning pins fitted in the round holes and positioning pins inserted in the elongated grooves.

* * * * *